US 7,785,275 B2

(12) United States Patent
Melsheimer (10) Patent No.: US 7,785,275 B2
(45) Date of Patent: Aug. 31, 2010

(54) WIRE GUIDE HAVING DISTAL COUPLING TIP

(75) Inventor: Jeffry S. Melsheimer, Springville, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/699,174

(22) Filed: Jan. 29, 2007

(65) Prior Publication Data

US 2007/0185416 A1    Aug. 9, 2007

Related U.S. Application Data

(60) Provisional application No. 60/763,511, filed on Jan. 31, 2006.

(51) Int. Cl.
*A61B 5/00* (2006.01)
(52) U.S. Cl. .................. 600/585; 604/264; 439/397
(58) Field of Classification Search .................. 600/585
See application file for complete search history.

(56) References Cited

U.S. PATENT DOCUMENTS

| | | | |
|---|---|---|---|
| 2,657,691 | A | 11/1953 | Nordstrom, Jr. |
| 3,521,620 | A | 7/1970 | Cook |
| 3,547,103 | A | 12/1970 | Cook |
| 3,656,680 | A | 4/1972 | Nomura |
| 3,739,784 | A | 6/1973 | Itoh |
| 3,890,997 | A | 6/1975 | Wilson |
| 4,548,206 | A | 10/1985 | Osborne |
| 4,569,347 | A | 2/1986 | Frisbie |
| 4,601,713 | A | 7/1986 | Fuqua |
| 4,650,472 | A | 3/1987 | Bates |
| 4,665,906 | A | 5/1987 | Jervis |
| 4,824,435 | A | 4/1989 | Giesy et al. |
| 4,921,483 | A | 5/1990 | Wijay et al. |
| 4,925,445 | A | 5/1990 | Sakamoto et al. |
| 4,934,380 | A | 6/1990 | De Toledo |
| 4,984,581 | A | 1/1991 | Stice |
| 5,003,990 | A | 4/1991 | Osypka |

(Continued)

FOREIGN PATENT DOCUMENTS

EP    0 436 303 A1    11/1990

(Continued)

OTHER PUBLICATIONS

International Search Report & Written Opinion (Jan. 3, 2008).

(Continued)

*Primary Examiner*—Max Hindenburg
*Assistant Examiner*—Renee Danega
(74) *Attorney, Agent, or Firm*—Brinks Hofer Gilson & Lione (57) ABSTRACT

A coupling wire guide is structured to be slidably coupled to a previously introduced wire guide, and is also well suited for stand-alone use. The coupling wire guide generally includes a main body having a distal end and a coupling tip connection to the distal end. The coupling tip includes a coupling portion and a tip portion. The coupling portion defines a coupling passageway having a proximal port and distal port for receiving a previously introduced wire guide. The tip portion includes a distal end surface having an atraumatic shape.

28 Claims, 5 Drawing Sheets

U.S. PATENT DOCUMENTS

| | | | |
|---|---|---|---|
| 5,046,497 A * | 9/1991 | Millar | 600/309 |
| 5,069,226 A | 12/1991 | Yamauchi et al. | |
| 5,105,818 A | 4/1992 | Christian et al. | |
| 5,129,890 A | 7/1992 | Bates et al. | |
| 5,131,407 A | 7/1992 | Ischinger et al. | |
| 5,159,861 A | 11/1992 | Anderson | |
| 5,213,111 A | 5/1993 | Cook et al. | |
| 5,234,003 A | 8/1993 | Hall | |
| 5,242,759 A | 9/1993 | Hall | |
| 5,243,996 A | 9/1993 | Hall | |
| 5,251,640 A | 10/1993 | Osborne | |
| 5,267,958 A | 12/1993 | Buchbinder et al. | |
| 5,306,261 A | 4/1994 | Alliger et al. | |
| 5,318,527 A | 6/1994 | Hyde et al. | |
| 5,325,746 A | 7/1994 | Anderson | |
| 5,328,472 A | 7/1994 | Steinke et al. | |
| 5,328,480 A | 7/1994 | Milker et al. | |
| 5,344,413 A | 9/1994 | Allman et al. | |
| 5,354,257 A | 10/1994 | Roubin et al. | |
| 5,383,853 A * | 1/1995 | Jung et al. | 604/103.04 |
| 5,395,332 A * | 3/1995 | Ressemann et al. | 604/103.1 |
| 5,402,799 A | 4/1995 | Colon et al. | |
| 5,449,362 A | 9/1995 | Chaisson et al. | |
| 5,456,680 A * | 10/1995 | Taylor et al. | 606/2 |
| 5,488,959 A | 2/1996 | Ales | |
| 5,597,378 A | 1/1997 | Jervis | |
| 5,667,521 A | 9/1997 | Keown | |
| 5,738,667 A | 4/1998 | Solar | |
| 5,762,070 A | 6/1998 | Nagamatsu | |
| 5,776,079 A | 7/1998 | Cope et al. | |
| 5,776,100 A * | 7/1998 | Forman | 604/102.03 |
| 5,797,857 A | 8/1998 | Obitsu | |
| 5,810,876 A | 9/1998 | Kelleher | |
| 5,827,225 A | 10/1998 | Ma Schwab | |
| 5,873,842 A * | 2/1999 | Brennen et al. | 600/585 |
| 5,882,333 A | 3/1999 | Schaer et al. | |
| 5,891,056 A | 4/1999 | Ramzipour | |
| 5,893,868 A | 4/1999 | Hanson et al. | |
| 5,993,424 A | 11/1999 | Lorenzo et al. | |
| 5,997,526 A | 12/1999 | Giba et al. | |
| 6,007,517 A | 12/1999 | Anderson | |
| 6,139,510 A | 10/2000 | Palermo | |
| 6,217,567 B1 | 4/2001 | Zadno-Azizi et al. | |
| 6,221,066 B1 | 4/2001 | Ferrera et al. | |
| 6,248,092 B1 | 6/2001 | Miraki et al. | |
| 6,254,549 B1 | 7/2001 | Ramzipoor | |
| 6,254,550 B1 | 7/2001 | McNamara et al. | |
| 6,290,693 B1 | 9/2001 | Jung, Jr. et al. | |
| 6,306,141 B1 | 10/2001 | Jervis | |
| 6,309,404 B1 | 10/2001 | Krzyzanowski | |
| 6,348,041 B1 | 2/2002 | Klint | |
| 6,348,045 B1 | 2/2002 | Malonek et al. | |
| 6,383,146 B1 | 5/2002 | Klint | |
| 6,471,697 B1 * | 10/2002 | Lesh | 606/41 |
| 6,475,167 B1 | 11/2002 | Fleming et al. | |
| 6,500,130 B2 | 12/2002 | Kinsella et al. | |
| 6,502,606 B2 | 1/2003 | Klint | |
| 6,517,518 B2 * | 2/2003 | Nash et al. | 604/164.02 |
| 6,530,899 B1 | 3/2003 | Savage | |
| 6,569,151 B1 | 5/2003 | Nash et al. | |
| 6,596,963 B2 | 7/2003 | Kelly | |
| 6,605,049 B1 | 8/2003 | Wagner et al. | |
| 6,613,002 B1 | 9/2003 | Clark et al. | |
| 6,638,372 B1 | 10/2003 | Abrams et al. | |
| 6,682,608 B2 | 1/2004 | Abrams et al. | |
| 6,805,676 B2 | 10/2004 | Klint | |
| 6,872,192 B2 | 3/2005 | Nash et al. | |
| 7,074,197 B2 | 7/2006 | Reynolds et al. | |
| 7,076,285 B2 * | 7/2006 | Windheuser et al. | 600/434 |
| 7,229,431 B2 | 6/2007 | Houser et al. | |
| 7,527,606 B2 * | 5/2009 | Oepen | 604/103.04 |
| 2002/0058888 A1 | 5/2002 | Biagtan et al. | |
| 2002/0169457 A1 | 11/2002 | Quinn | |
| 2003/0028127 A1 | 2/2003 | Balzum et al. | |
| 2003/0120208 A1 | 6/2003 | Houser et al. | |
| 2004/0073108 A1 * | 4/2004 | Saeed et al. | 600/431 |
| 2004/0116957 A1 | 6/2004 | Nishide | |
| 2004/0199087 A1 | 10/2004 | Swain et al. | |
| 2004/0215208 A1 | 10/2004 | Foushee et al. | |
| 2005/0027212 A1 | 2/2005 | Segner et al. | |
| 2005/0075647 A1 | 4/2005 | Walters et al. | |
| 2005/0143770 A1 | 6/2005 | Carter et al. | |
| 2005/0148902 A1 | 7/2005 | Minar et al. | |
| 2005/0197663 A1 | 9/2005 | Soma et al. | |
| 2005/0209533 A1 * | 9/2005 | Lorenz | 600/585 |
| 2005/0267442 A1 | 12/2005 | Von Oepen | |
| 2005/0283122 A1 | 12/2005 | Nordgren | |
| 2006/0020256 A1 | 1/2006 | Bell et al. | |
| 2006/0100544 A1 | 5/2006 | Ayala et al. | |
| 2006/0100545 A1 | 5/2006 | Ayala et al. | |
| 2007/0060908 A1 | 3/2007 | Webster et al. | |
| 2007/0149946 A1 | 6/2007 | Viswanathan et al. | |
| 2007/0167065 A1 | 7/2007 | Melsheimer et al. | |
| 2007/0185414 A1 | 8/2007 | Urbanski et al. | |
| 2007/0191790 A1 | 8/2007 | Eells et al. | |

FOREIGN PATENT DOCUMENTS

| | | | |
|---|---|---|---|
| EP | 0829269 A1 | | 3/1998 |
| EP | 1057500 A1 | | 12/2000 |
| EP | 1 428 546 A2 | | 6/2004 |
| WO | WO 93/14805 | | 8/1993 |
| WO | WO 96/10436 | | 4/1996 |
| WO | WO 99/44510 | | 9/1999 |
| WO | WO 00/74565 A1 | | 12/2000 |
| WO | WO/01/03764 | * | 1/2001 |
| WO | WO 01/03764 A1 | | 1/2001 |
| WO | WO 02 094364 A2 | | 11/2002 |
| WO | WO2004/033016 | | 4/2004 |
| WO | WO 2004/049970 A2 | | 6/2004 |
| WO | WO 2004/050161 A1 | | 6/2004 |
| WO | WO 2005/011530 A1 | | 2/2005 |
| WO | WO 2005/011788 A1 | | 2/2005 |
| WO | WO 2005/025660 A1 | | 3/2005 |
| WO | WO 2005/089852 A1 | | 9/2005 |
| WO | WO 2006/039216 A2 | | 4/2006 |
| WO | WO 2007/084474 A1 | | 7/2007 |
| WO | WO 2007/089891 A1 | | 8/2007 |
| WO | WO 2007/089893 | | 8/2007 |

OTHER PUBLICATIONS

Notification of Transmittal of International Preliminary Report on Patentability (Jan. 3, 2008).

The Journal of Invasive Cardiology entitled "Use of a Second Buddy Wire During Percutaneous Coronary Interventions: A Simple Solution for Some Challenging Situations" dated Apr. 25, 2005, pp. 1-8.

International Search Report—PCT/US2006/040843 (Jan. 31, 2007.

International Search Report—PCT/US2007/002743 (Jun. 14, 2007).

International Search Report—PCT/US2007/002741 ( Jul. 9, 2007).

International Search Report—PCT/US2006/042184 (Mar. 1, 2007).

International Search Report — PCT/US2007/001066 (Jun. 18, 2007).

International Search Report—PCT/US2007/004827 (Oct. 26, 2007).

Office Action dated Nov. 15, 2007 issued in related U.S. Appl. No. 11/652,430.

Office Action dated Mar. 17, 2008 U.S. Appl. No. 11/706,548 issued in related application.

Office Action dated May 16, 2008 U.S. Appl. No. 11/763,355 issued in related application.

Office Action dated May 30, 2008 U.S. Appl. No. 11/507,805 issued in related application.

Office Action dated May 23, 2008 U.S. Appl. No. 11/652,430 issued in related application.

International Search Report—PCT/US2007/04827 & Opinion (Mar. 14, 2008).
Suppl) Notification of Transmittal of International Preliminary Report on Patentability—PCT/US2007/002743—(Jun. 3, 2008).
Office Action Restriction dated Mar. 3, 2008 U.S. Appl. No. 11/507,805 issued in related application.
Office Action Restriction dated Jul. 2, 2008 U.S. Appl. No. 11/699,171 issued in related application.
International Search Report/Written Opinion—PCT/US2006/040843 (Feb. 7, 2007).
International Preliminary Report on Patentability—PCT/US2007/002741 (Jun. 25, 2008).
Office Action dated Oct. 20, 2008 U.S. Appl. No. 11/549,481 issued in co-pending application.
Office Action dated Oct. 28, 2008 U.S. Appl. No. 11/507,805 issued in co-pending application.
Office Action dated Nov. 20, 2008 U.S. Appl. No. 11/763,355 issued in co-pending application.
Office Action dated Nov. 21, 2008 U.S. Appl. No. 11/549,473 issued in co-pending application.
Office Action dated Nov. 21, 2008 U.S. Appl. No. 11/699,171 issued in co-pending application.
Office Action dated Dec. 11, 2008 U.S. Appl. No. 11/652,430 issued in co-pending application.
Advisory Action dated Jan. 16, 2009 U.S. Appl. No. 11/507,805 issued in co-pending application.
International Preliminary Report on Patentability and Written Opinion (Jul. 24, 2008) PCT/US2007/001066.
Office Action dated Sep. 26, 2008 U.S. Appl. No. 11/706,548 issued in related application.
Office Action dated Oct. 7, 2008 U.S. Appl. No. 11/507,993 issued in related application.
Advisory Action dated Mar. 6, 2009 U.S. Appl. No. 11/652,430 issued in co-pending application.
Office Action dated Apr. 1, 2009 U.S. Appl. No. 11/507,805 issued in co-pending application.
Office Action dated Apr. 7, 2009 U.S. Appl. No. 11/706,548 issued in co-pending application.
Office Action dated Apr. 14, 2009 U.S. Appl. No. 11/549,481 issued in co-pending application.
Office Action dated May 8, 2009 U.S. Appl. No. 11/699,171 issued in co-pending application.
Office Action dated May 14, 2009 U.S. Appl. No. 11/507,993 issued in coo-pending application.
Office Action dated Jun. 9, 2009 U.S. Appl. No. 11/763,355 issued in co-pending application.
Advisory Action dated Jun. 25, 2009 U.S. Appl. No. 11/549,481 issued in co-pending application.
Advisory Action dated Jun. 22, 2009 U.S. Appl. No. 11/706,548 issued in co-pending application.
Office Action dated Jun. 23, 2009 U.S. Appl. No. 11/652,430 issued in co-pending application.
Office Action dated Sep. 16, 2009 U.S. Appl. No. 11/549,481 issued in co-pending application.
Office Action dated Oct. 1, 2009 U.S. Appl. No. 11/763,355 issued in co-pending application.
Office Action dated Oct. 14, 2009 U.S. Appl. No. 11/507,805 issued in co-pending application.
Office Action dated Oct. 23, 2009 U.S. Appl. No. 11/706,548 issued in co-pending application.
Office Action dated Dec. 9, 2009 U.S. Appl. No. 11/652,430 issued in co-pending application.
Office Action dated Dec. 14, 2009 U.S. Appl. No. 11/507,993 issued in co-pending application.
Office Action dated Jan. 19, 2010 U.S. Appl. No. 11/699,171 issued in co-pending application.
Office Action dated Apr. 2, 2010 U.S. Appl. No. 11/507,805 issued in co-pending application.
Office Action dated Apr. 6, 2010 U.S. Appl. No. 11/763,355 issued in co-pending application.
Office Action dated Jun. 4, 2009 U.S. Appl. No. 11/549,473 issued in co-pending application.

* cited by examiner

WIRE GUIDE HAVING DISTAL COUPLING TIP

CROSS-REFERENCE TO RELATED APPLICATIONS

This application claims the benefit of U.S. Provisional Application Ser. No. 60/763,511 filed on Jan. 31, 2006, entitled "WIRE GUIDE HAVING DISTAL COUPLING TIP", the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for intracorporeal procedures that may be easily and reliably traversed to a position proximate a previously introduced wire guide.

BRIEF SUMMARY OF THE INVENTION

The present invention provides a supporting wire guide for intracorporeal procedures that may be easily and reliably traversed to a position proximate a previously introduced wire guide, as well as be used as a stand-alone wire guide. The supporting wire guide is a coupling wire guide that is structured to be slidably coupled to the previously introduced wire guide. In one embodiment constructed in accordance with the teachings of the present invention, the coupling wire guide generally includes a main body having a distal end and a coupling tip connected to the distal end. The coupling tip includes a coupling portion and a tip portion. The tip portion includes a distal end surface having an atraumatic shape. The coupling portion defines a coupling passageway having a proximal port and distal port. Both the proximal and distal ports open radially. In this manner, the coupling wire guide is well suited for use as a stand-alone wire guide, as well as being capable of being coupled to a previously introduced wire guide.

According to more detailed aspects of the invention, the coupling tip is coaxial with the main body and preferably has an outer diameter about equal to or less than an outer diameter of the main body. These features permit the coupling wire guide to be withdrawn proximally through a catheter or other device which is placed over the coupling wire guide. The proximal and distal ports may be circumferentially aligned or non-aligned. When not aligned, the proximal and distal ports preferably open radially in opposite directions. The proximal and distal ports preferably span an axial distance greater than about three times the diameter of the previously introduced wire guide. The coupling wire guide may further include intermediate and distal end caps adjacent the proximal and distal ports, respectively, which define a guiding surface structured to guide the previously introduced wire guide relative to the respective port.

According to additional detailed aspects of the invention, the coupling wire guide may further include means for directly attaching the coupling portion to the previously introduced wire guide at a point between the ends of the previously introduced wire guide. Accordingly, the coupling wire guide may be "clipped-on" to the mid-section of the previously introduced wire guide or at any location having the most efficacy. This attachment function may include constructing the coupling portion of a resilient material having a slot extending from the proximal port to the distal port. Alternatively, the attachment means may include forming the coupling portion as a helically wound strip.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
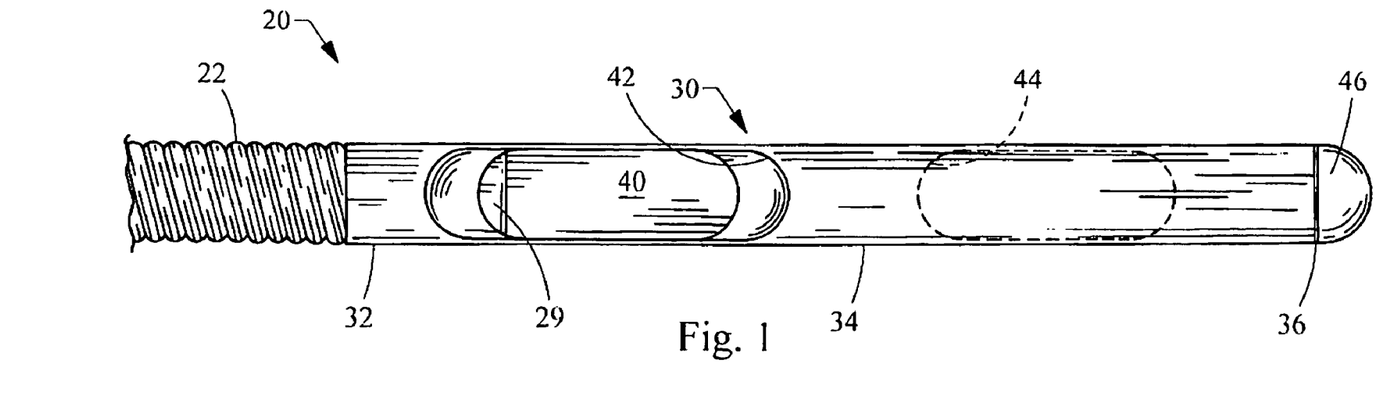
FIG. 1 is a top view of a coupling wire guide constructed in accordance with the teachings of the present invention.
Figure 2:
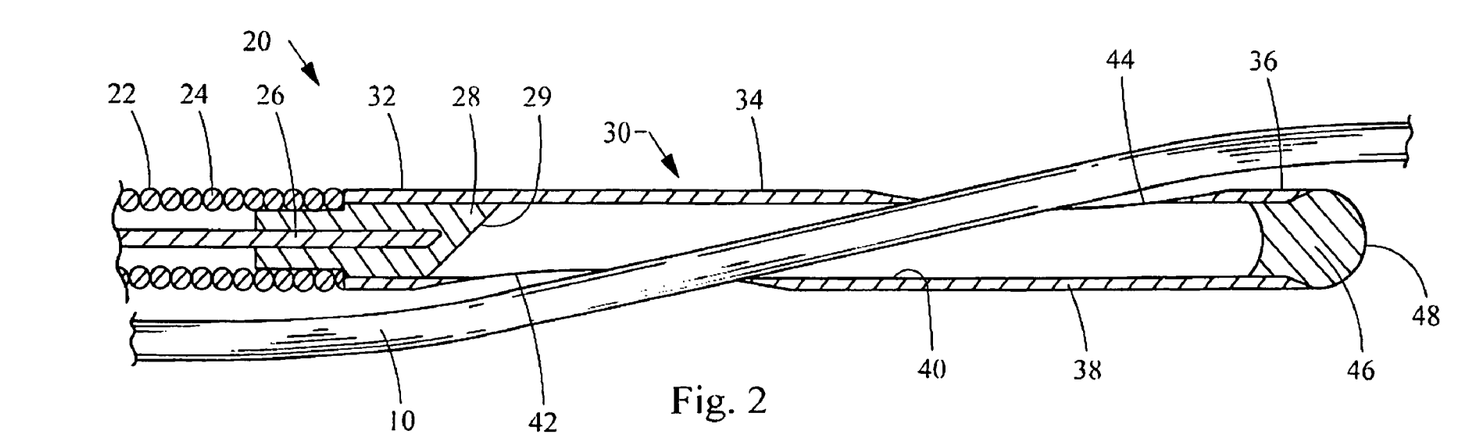
FIG. 2 is a cross-sectional view of the coupling wire guide depicted in FIG. 1.

Turning now to the figures, FIGS. 1 and 2 depict a coupling wire guide 20 constructed in accordance with the teachings of the present invention. The coupling wire guide 20 is easily and reliably coupled to and traversed along a previously introduced wire guide 10 (FIG. 2), and notably is well suited for serving as a standard wire guide when not coupled to the previously introduced wire guide 10. Specifically, the distal end includes an atraumatic configuration facilitating stand-alone use, while the coupling wire guide 20 maintains the ability to be withdrawn proximally through a device placed over it, such as catheter devices, angioplasty devices, stenting devices, embolic protection devices, filtering devices, biopsy devices, cooling/aspiration devices and many other medical devices which may be tracked over a wire guide. While wire guides are generally used in percutaneous interventional procedures, it will be recognized by those skilled in the art that the wire guide 20 of the present invention may also be employed non-percutaneously, such as in endoscopic or other intracorporeal procedures.

The coupling wire guide 20 generally includes a main body 22 having a coiled wire 24 disposed over a mandrel 26, a structure well known in the art. An end cap 28 forms the distal end of the main body 22, and includes a guiding surface 29 structured to guide the previously introduced wire guide 10 relative to the coupling tip 30. It will be recognized that the main body 22 of the coupling wire guide 20, as well as the previously introduced wire guide 10, may take numerous forms as many types of wire guides are known in the art, including solid wire, tubular wires, coiled wires and combinations thereof. For example, U.S. Pat. No. 5,243,996 discloses an exemplary solid wire mandrel having a coiled tip section, the disclosure of which is hereby incorporated by reference in its entirety.

Preferably, the coupling tip 30 is constructed of a resilient material such as nitinol (nickel-titanium superelastic alloy) or stainless steel, although any biocompatible resilient material may be employed including thermoplastics and other metals or alloys. The coupling tip 30 may be formed by laser cutting or otherwise removing material from a tubular cannula. As such, the main body 22 could be unitarily formed with the coupling tip 30 and the main body 22 could simply comprise the tubular structure of the coupling tip 30 extended proximally. Such a tubular body 22 could further include slots or notches which improve the flexibility of the tubular cannula.

The coupling tip 30 includes an attachment portion 32, a coupling portion 34, and a tip portion 36. The coupling tip 30 is generally formed out of a tubular structure 38, and preferably by laser cutting a cannula as noted above. The use of a tubular structure 38 provides the coupling tip 30 with sufficient axial rigidity and radial flexibility for navigation of the vasculature either attached to the previously introduced wire guide 10 or as an individual wire guide 20.

As best seen in FIG. 2, the coupling tip 30 is preferably attached to the distal end of main body 22 by soldering or welding the tubular attachment portion 32 of the coupling tip 30 to the intermediate end cap 28 of the main body 22 (and to the outer wire 24). As the main body 22 and the coupling tip 30 may be constructed of numerous types of materials, it will be recognized that numerous types of attachment structures or methods may be employed such as adhesives, fasteners, material deformation, latches, plastic welding techniques and the like. The outer diameter of the coupling tip 30, and at least the attachment portion 32, is about equal to or less than a diameter of the main body 22. Due to the similarly sized outer diameters, the coupling wire guide 20 may be proximally withdrawn from any device which is placed over the wire guide 20, further enhancing the stand-alone use of the coupling wire guide 20. As a result, the coupling tip 30 will have an outer diameter greater than the outer diameter of the previously introduced wire guide 10, and an inside diameter compatible with the outer diameter of the previously introduced wire guide 10.

The coupling portion 34 defines a coupling passageway 40 having a proximal port 42 and a distal port 44 through which the previously introduced wire guide 10 passes during the Buddy Wire or related techniques. The proximal and distal ports 42, 44 are radially facing openings (i.e. open radially) to provide access to the coupling passageway 40 while maintaining the outer diameter of the coupling tip 30. As such, the outer diameter of the coupling wire guide 20, and specifically the coupling tip 30, is greater than the previously introduced wire guide 10 to which it will be slideably coupled. In the embodiment depicted in FIGS. 1 and 2, the proximal and distal ports 42, 44 face in radially opposite directions, i.e., they are circumferentially spaced by about 180 degrees. Preferably the proximal and distal ports 42, 44 span an axial distance of about three times the outer diameter of the previously introduced wire guide 10 or more to facilitate a smooth transition of the wire guide 10 into the coupling passageway 40.

To further enhance the ability of the coupling wire guide 20 to serve as an individual wire guide when decoupled from the previously introduced wire guide 10, the tip portion 36 includes a distal end cap 46 defining an exposed distal end surface 48. The distal end cap 46 and its end surface 48 are structured atraumatically, and preferably as a spherical ball shape to assist in placement of the wire guide 20 and prevent damage to the vasculature. This feature of the coupling tip 30, in combination with the tubular structure 38 providing axial rigidity and radial flexibility, as well as the similarly sized outer diameters, makes the coupling wire guide 20 well suited for stand-alone use and coupling to a previously introduced wire guide 10. The distal end cap 46, as well as the intermediate end cap 28, are preferably formed from a solder material such as metal alloys (e.g. Tin-Silver-Copper), although many other materials, including thermoplastics, may readily be employed to form the end caps, which are then connected to the main body 22 and the coupling tip 30 through any of the methods described above.

Figure 3:
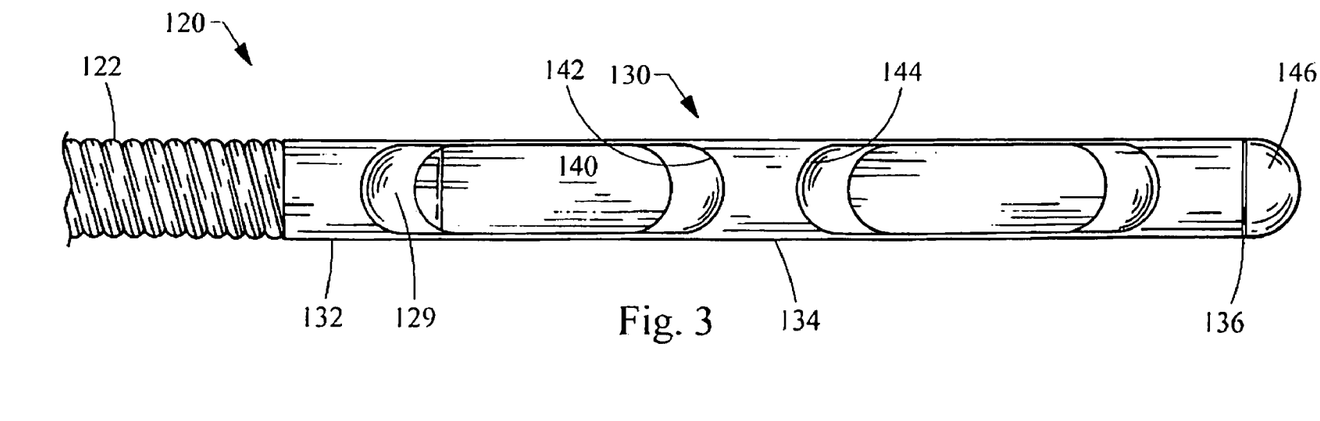
FIG. 3 is a top view of another embodiment of a coupling wire guide constructed in accordance with the teachings of the present invention.
Figure 4:
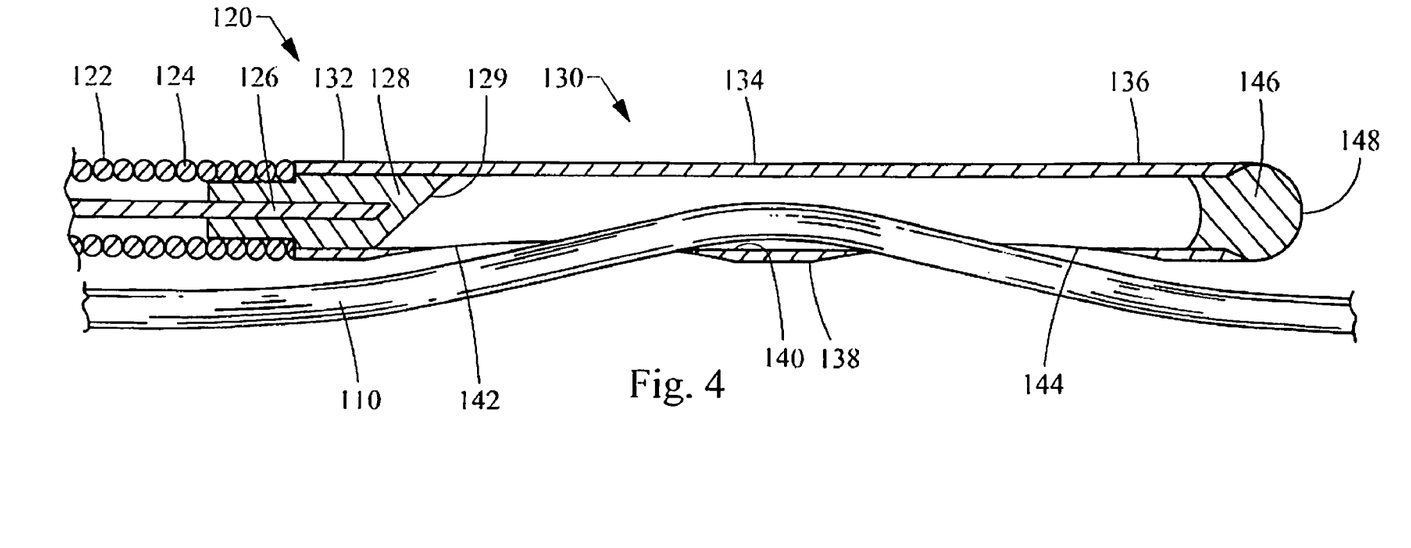
FIG. 4 is a cross-sectional view of the coupling wire guide depicted in FIG. 3.

It will be recognized by those skilled in the art that the proximal and distal ports 42, 44 may take many different configurations and relative positioning. For example, FIGS. 3 and 4 depict another embodiment of a coupling wire guide 120 having differently arranged proximal and distal ports 142, 144, in accordance with the teachings of the present invention. Similar to the previous embodiment, the coupling wire guide 120 includes a main body 122 having an outer wire 124 disposed over an inner mandrel 126 and secured at their distal end by an intermediate end cap 128. The intermediate end cap 128 defines a guiding surface 129 structured to guide the previously introduced guide wire 10 relative to the proximal port 144. A coupling tip 130 generally includes an attachment portion 132, a coupling portion 134 and a tip portion 136. The coupling tip 130 is constructed of a tubular member 138, and the coupling portion 134 defines a coupling passageway 140 having proximal port 142 and distal port 144 sized to receive a previously introduced wire guide 110 therein.

The coupling wire guide 120 and its coupling tip 130 are again provided with a distal end cap 146 defining an atraumatic end surface 148. It will also be noted that in this embodiment, the proximal port 142 and the distal port 144 are facing in the same radial direction. That is, the proximal and distal ports 142, 144 are circumferentially aligned, whereby the previously introduced wire guide 110 enters and exits the coupling tip 130 from the same side of the coupling wire guide 120. As noted above, the relative orientation of the proximal and distal ports 142, 144 may take many configurations, and FIGS. 1-4 merely depict two preferred configurations.

Figure 5:
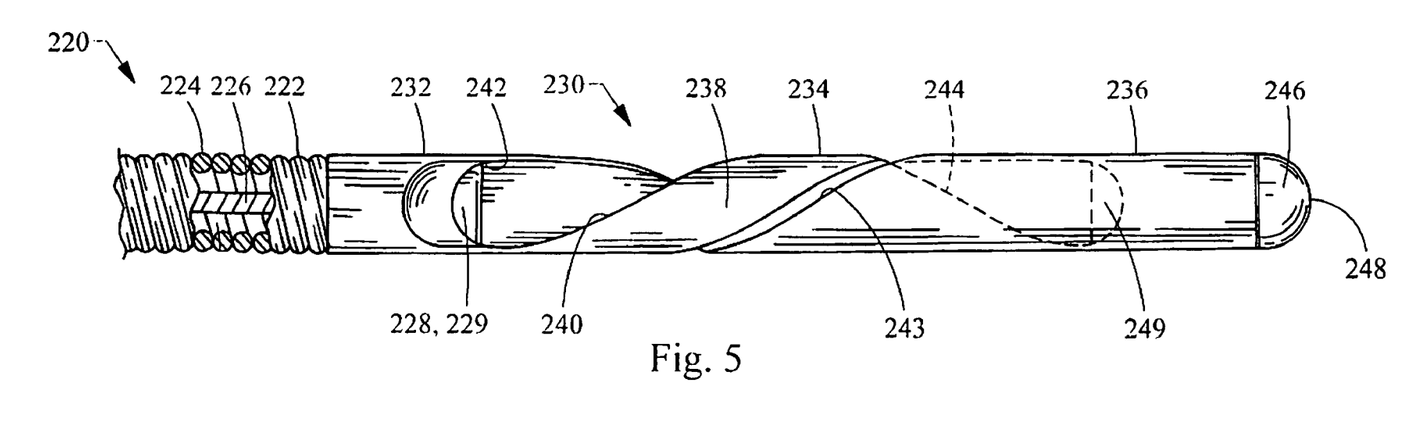
FIG. 5 is a top view of another embodiment of a coupling wire constructed in accordance with the teachings of the present invention.
Figure 6:
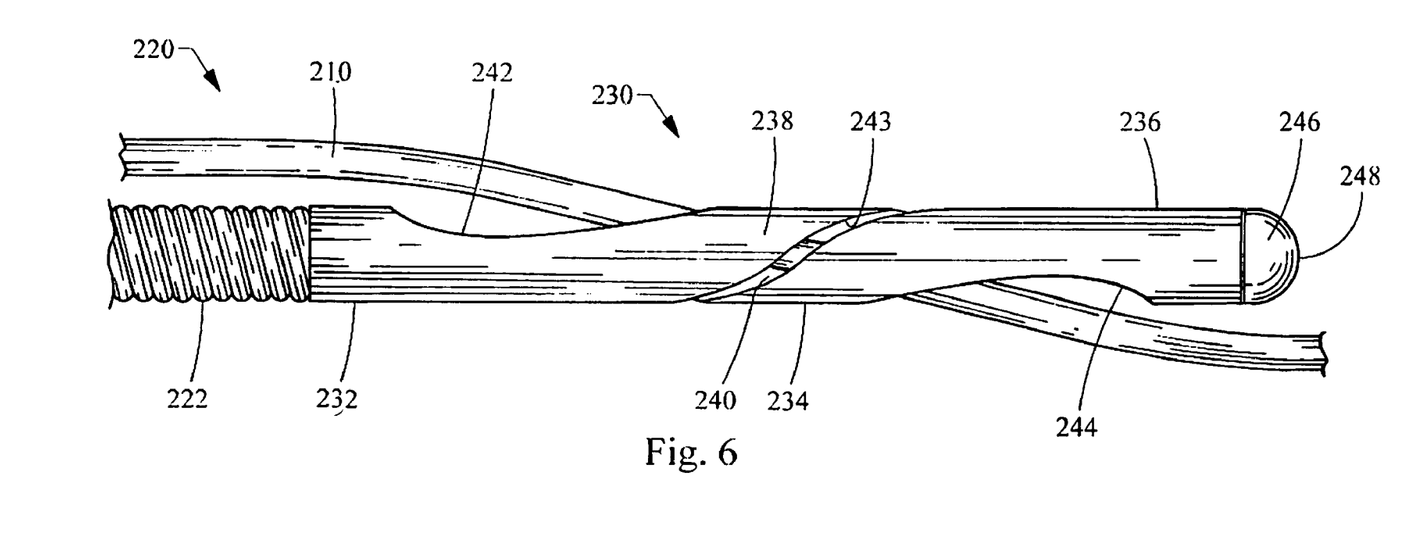
FIG. 6 is a side view of the coupling wire guide depicted in FIG. 5.

Turning now to FIGS. 5 and 6, depicted is another embodiment of a coupling wire guide 220 constructed in accordance with the teachings of the present invention. The coupling wire guide 220 is "side-loading", meaning the wire guide 220 may be attached by "clipping-on" to a mid-section of the previously introduced wire guide 10. As used herein, the term "mid-section" refers to any point between the free ends of the previously introduced wire guide. In this manner, the coupling wire guide 220 may be coupled to and traversed along the previously introduced wire guide 210 without gaining access to the proximal or distal end of the previously introduced wire guide 210, further increasing the versatility thereof.

As with the previous embodiments, the coupling wire guide 220 generally includes a main body 222 formed of an outer wire 224 disposed over an inner mandrel 226 which are linked at their distal ends by an intermediate end cap 228 defining a guide surface 229. A coupling tip 230 is connected to a distal end of the main body 222 and generally includes an attachment portion 232, a coupling portion 234 and a tip portion 236. The tip portion 236 again includes a distal end cap 246 defining a distal end surface 248 which is designed to be atraumatic. The coupling portion 234 defines an internal coupling passageway 240 having a proximal port 242 and a distal port 244 sized to receive the previously introduced wire guide 210. The distal end cap 246 defines a guide surface 249 for guiding the previously introduced wire guide 210 relative to the proximal port 244.

Unlike the prior embodiments, the coupling tip 230 includes a generally tubular member 238 having a helical slot 243 formed therein which is in communication with the coupling passageway 240. Further, the slot 243 extends from the proximal port 242 to the distal port 244, thereby providing the "side-loading" function to the coupling wire guide 220. That is, the previously introduced wire guide 210 may simply be pressed through the slot 243, which expands in size due to the resilient but flexible nature of the coupling tip 230. Alternatively, the coupling portion 234 may be thought of as a helically wound strip of material 238, which can be at least partially unwound and then rewound around the previously introduced wire guide 210.

It will be recognized by those skilled in the art that the structure of the slot 243 extending between the proximal and distal ports 242, 244 can take many forms, as can the coupling portion 234, in order to provide "side-loading" of the coupling tip 230. For example, while the slot 243 has been shown generally smaller than a diameter of the previously introduced wire guide 210, the slot 243 may have a larger width and utilize features such as retaining tabs projecting into the area of the slot. Still further, the slot 243 may be linear (i.e. generally parallel to a central axis of the coupling tip 230) or curved, or helical as shown. Further details regarding various structures providing side-loading to a coupling tip having proximal and distal ports may be found in commonly assigned and copending U.S. Patent Application No. 60/763, 523, the disclosure of which is hereby incorporated by reference in its entirety.

Figure 7:
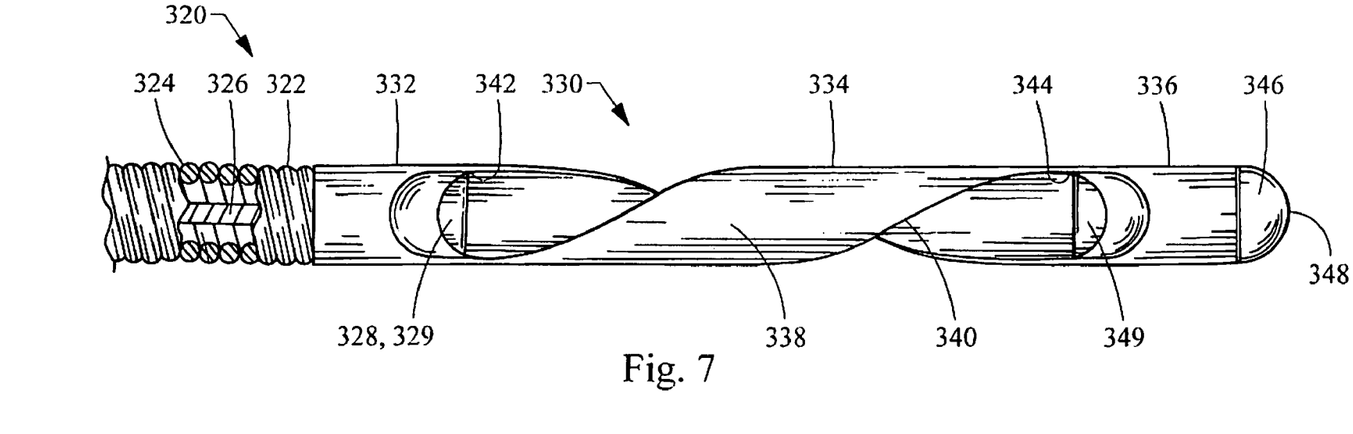
FIG. 7 is a top view of another embodiment of a coupling wire guide constructed in accordance with the teachings of the present invention.
Figure 8:
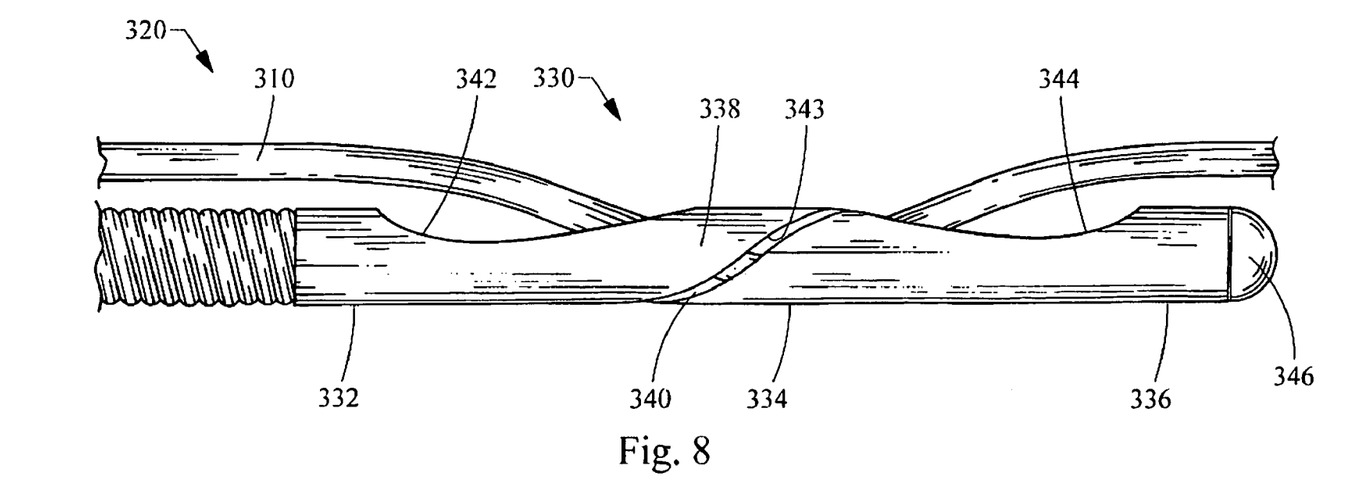
FIG. 8 is a side view of the coupling wire guide depicted in FIG. 7.

FIGS. 7 and 8 depict yet another embodiment of a coupling wire guide 320 constructed in accordance with the teachings of the present invention. As with the previously embodiments, the coupling wire guide 320 generally includes a main body 322 formed of an outer wire 324 disposed over an inner mandrel 326 and linked at their distal end by an intermediate end cap 328 defining a guide surface 329. A coupling tip 330 is connected to a distal end of the main body 322 and generally includes an attachment portion 332, a coupling portion 334 and a tip portion 336. The tip portion 336 again includes a distal end cap 346 defining a distal end surface 348 which is designed to be atraumatic. The distal end cap 346 also defines a guide surface 349 for guiding the previously introduced wire guide 310 relative to the proximal port 344. The coupling portion 334 is constructed of a generally tubular member 338 defining an internal coupling passageway 340 having a proximal port 342 and a distal port 344 sized to receive the previously introduced wire guide 310. A generally helical slot 343 in the coupling portion 334 provides the distal tip 330 with "side-loading" functionality, as discussed in the prior embodiment.

In the embodiments of FIGS. 5 and 6, the proximal and distal ports 242, 244 face in radially opposite directions. However, in this embodiment (FIGS. 7 and 8), the proximal and distal ports 342, 344 face in the same radial direction. That is, similar to the embodiment depicted in FIGS. 3 and 4, the proximal and distal ports 342, 344 are circumferentially aligned, permitting the previously introduced wire guide 310 to enter and exit the coupling passageway 340 from the same side of the coupling wire guide 320.

Figure 9:
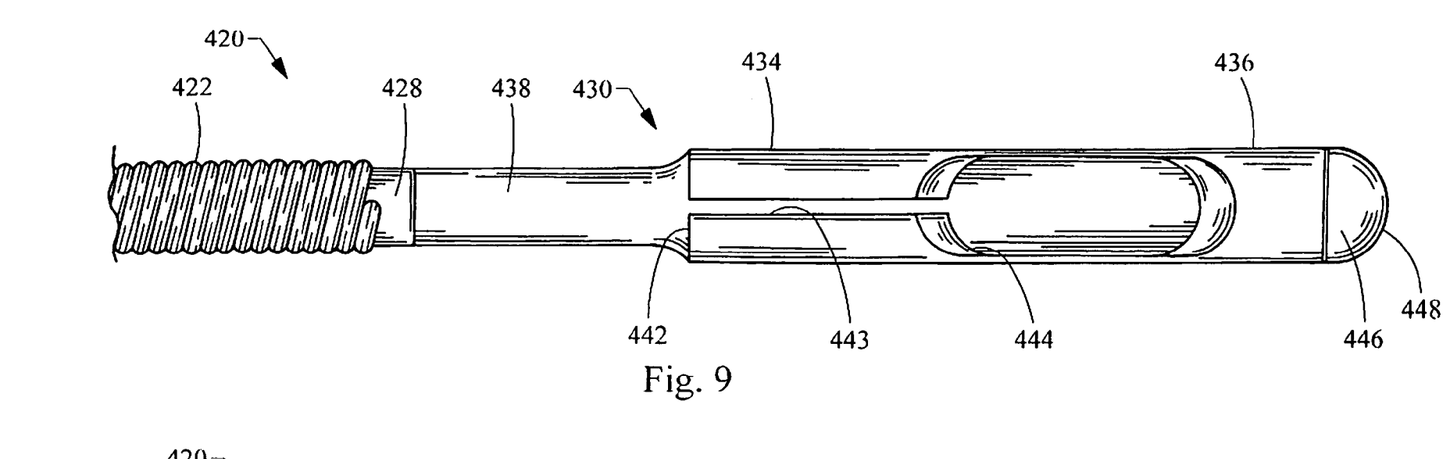
FIG. 9 is a top view of another embodiment of a coupling wire guide constructed in accordance with the teachings of the present invention.
Figure 10:
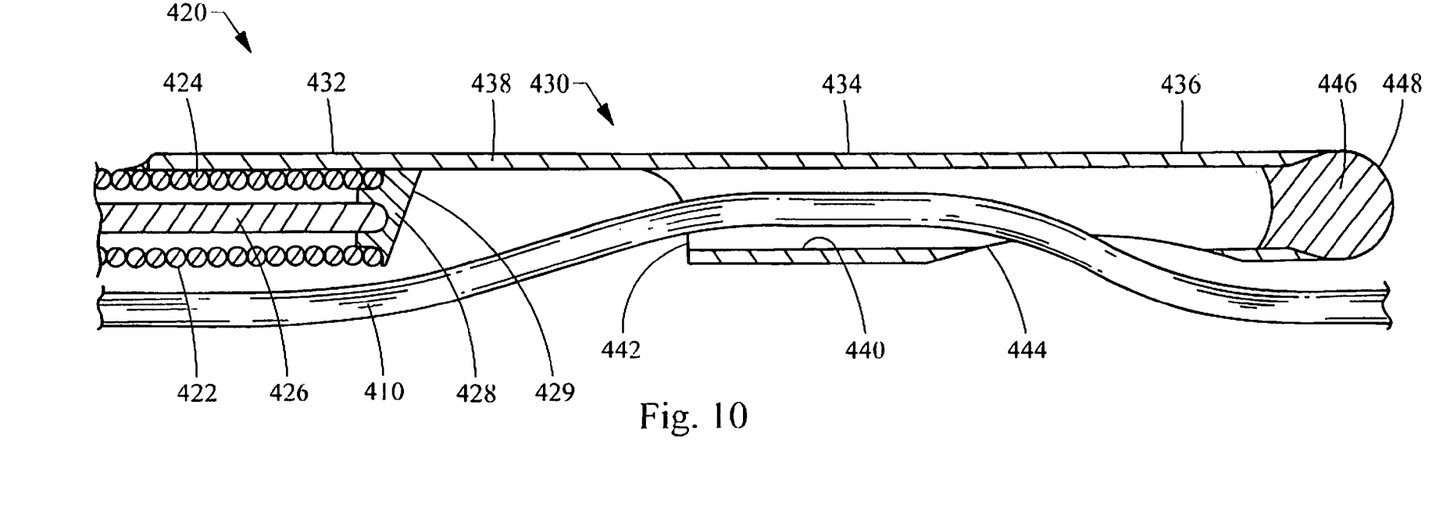
FIG. 10 is a cross-sectional view of the coupling wire guide depicted in FIG. 9.

Another embodiment of a coupling wire guide 420 constructed in accordance with the teachings of the present invention has been depicted in FIGS. 9 and 10. As with the previous embodiments, the coupling wire guide 420 includes the main body 422 having an outer wire 424 disposed over an inner mandrel 426 and linked at their distal ends by an intermediate end cap 428 defining a guiding surface 429. A coupling tip 430 generally includes an attachment portion 432, a coupling portion 434 and a tip portion 436. In this embodiment, the attachment portion 432 is formed of a strip of material 438 having a semi-annular cross-section, preferably spanning about 90 degrees. As such, the semi-annular strip 438 is attached to the distal end of the main body 422 by soldering or welding directly to the outer coil 424 and intermediate end cap 428.

The coupling portion 434 of the coupling tip 430 is constructed of a tubular member defining a coupling passageway 440 having proximal port 442 and a distal port 444 sized to receive the previously introduced wire guide 410. Unlike the prior embodiments, in this embodiment the proximal port 442 is axially facing. More particularly, the semi-annular strip 438 forming the attachment portion 432 extends axially from the distal end of the main body 422 a distance before the coupling portion 434 having a tubular structure. The distal port 444 is constructed similarly to prior embodiments and opens radially. Likewise, the tip portion 436 is constructed similarly to previous embodiments and includes a distal end cap 446 defining a distal end surface 448 that is atraumatic.

By providing an attachment portion 432 formed as a strip 438, the coupling tip 430 may be connected to an already existing wire guide while only minimally increasing its outer diameter, maintaining the ability to be withdrawn proximally from a device placed over the coupling wire guide 420. A linear slot 443 has also been provided linking the proximal port 442 to the distal port 444, thereby providing a "side-loading" function as previously discussed. Generally, the coupling tip 430 is constructed of a resilient material which flexes to adjust the size of the slot 443 to permit passageway of the previously introduced wire guide 410 therethrough.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for coupling to a previously introduced wire guide during intracorporeal procedures, the coupling wire guide comprising:
    a main body having a distal end defining a longitudinal axis, the distal end having a closed distal end surface;
    a coupling tip connected to the distal end of the main body, the coupling tip including an elongated tubular member having an attachment portion, a coupling portion and a tip portion;
    the tip portion including a closed distally facing end surface having an atraumatic shape; and
    the coupling portion including a cylindrical wall defining a coupling passageway having a proximal port and a distal port, the proximal and distal ports being spaced away from the proximal and distal ends of the elongated tubular member, respectively, the proximal and distal ports both opening radially and being elongated in a longitudinal direction, the proximal and distal ports each spanning an axial distance greater than about three times the diameter of the previously introduced wire guide.

2. The coupling wire guide of claim 1, wherein the coupling tip has an outer diameter about equal to or less than an outer diameter of the main body.

3. The coupling wire guide of claim 1, wherein the coupling tip is co-axial with the main body.

4. A coupling wire guide for coupling to a previously introduced wire guide during intracorporeal procedures, the coupling wire guide comprising:
    a main body having a closed distal end defined by an intermediate end cap;
    a coupling tip connected to the distal end of the main body, the coupling tip having a tubular member including a coupling portion and a tip portion;
    the tip portion including a distal end surface having an atraumatic shape; and
    the coupling portion defining a coupling passageway having a proximal port and a distal port, the proximal and distal ports both opening radially, the main body extending through the tubular member such that the intermediate end cap is positioned proximate the proximal port, the intermediate end cap defining a guiding surface exposed to the proximal port and structured to engage and guide the previously introduced wire guide relative to the proximal port.

5. The coupling wire guide of claim 1, wherein the proximal and distal ports are circumferentially aligned to face outward in the same radial direction.

6. The coupling wire guide of claim 1, wherein the proximal and distal ports open radially in radially opposite directions.

7. The coupling wire guide of claim 4, wherein the proximal and distal ports each span an axial distance greater than three times the diameter of the previously introduced wire guide.

8. The coupling wire guide of claim 1, wherein the distal end of the main body includes an intermediate end cap, the intermediate end cap defining a guiding surface exposed to the proximal port and structured to engage and guide the previously introduced wire guide relative to the proximal port.

9. The coupling wire guide of claim 1, wherein the tip portion includes a distal end cap defining the distal end surface, the distal end cap defining an interior guiding surface exposed to the distal port and structured to engage and guide the previously introduced wire guide relative to the distal port.

10. The coupling wire guide of claim 1, further comprising an attachment means for directly attaching the coupling portion to the previously introduced wire guide at a point between the ends of the previously introduced wire guide and retaining the previously introduced wire guide within the coupling passageway during relative translation of the coupling wire guide and previously introduced wire guide.

11. The coupling wire guide of claim 10, wherein the attachment means comprises a slot formed in the coupling portion extending from the proximal port to the distal port, the slot being in communication with the coupling passageway.

12. The coupling wire guide of claim 10, wherein the coupling portion comprises a helically wound strip that is configured to form the attachment means.

13. A coupling wire guide for coupling to a previously introduced wire guide during intracorporeal procedures, the coupling wire guide comprising:

a main body having a distal end and defining a longitudinal axis;
a coupling tip connected to the distal end of the main body, the coupling tip including a coupling portion and a tip portion;
the tip portion including a closed distally facing end surface; and
the coupling portion defining a coupling passageway having a proximal port and a distal port, the proximal port opening axially and being coaxial with the longitudinal axis at the distal end of the main body, the distal port spaced from the distal end surface and opening radially.

14. The coupling wire guide of claim 13, the coupling tip further including an attachment portion connected to the main body, the attachment portion structured as a semi-annular strip extending longitudinally parallel to the distal end of the main body.

15. The coupling wire guide of claim 13, wherein the coupling portion is formed by a tubular member having a cylindrical wall defining the coupling passageway and the proximal and distal ports.

16. The coupling wire guide of claim 13, wherein the coupling portion is formed by a helical strip.

17. The coupling wire guide of claim 16, wherein the coupling portion is constructed of a resilient material, the helical strip flexing to receive the previously introduced wire guide.

18. The coupling wire guide of claim 16, wherein the helical strip is structured for partial un-winding and re-winding around the previously introduced wire guide.

19. The coupling wire guide of claim 13, further comprising a slot formed in the coupling tip, the slot in communication with the coupling passageway and extending from the proximal port to the distal port, the slot having a width less than a diameter of the previously introduced wire guide.

20. The coupling wire guide of claim 13, wherein the coupling tip has an outer diameter about equal to or less than an outer diameter of the main body.

21. The coupling wire guide of claim 20, wherein the main body has an outer diameter greater than an outer diameter of the previously introduced wire guide, and wherein the coupling passageway has a diameter greater than or equal to the outer diameter of the previously introduced wire guide.

22. The coupling wire guide of claim 1, wherein the closed distal end surface of the tip portion has a semi-spherical shape.

23. The coupling wire guide of claim 4, wherein the tubular member defines a longitudinal axis, and wherein the guiding surface is angled relative to the longitudinal axis.

24. The coupling wire guide of claim 13, wherein the distal port spans an axial distance greater than about three times the diameter of the previously introduced wire guide.

25. The coupling wire guide of claim 4, wherein the distal end defines a longitudinal axis, and wherein the proximal and distal ports are longitudinally aligned around the circumference of the coupling portion.

26. The coupling wire guide of claim 1, wherein the distal end of the main body extends through the attachment portion of the elongated tubular member to a position where the closed distal end surface is proximate the proximal port to engage and guide the previously introduced wire guide relative to the proximal port.

27. The coupling wire guide of claim 26, wherein the closed distal end surface is longitudinally aligned with the proximal port.

28. The coupling wire guide of claim 4, wherein the guiding surface is longitudinally aligned with the proximal port.

* * * * *